(12) United States Patent
Eitan et al.

(10) Patent No.: US 8,098,372 B2
(45) Date of Patent: Jan. 17, 2012

(54) OPTICAL INSPECTION TOOL FEATURING MULTIPLE SPEED MODES

(75) Inventors: Giora Eitan, Reovot (IL); Shai Silberstein, Rishon-Le-Zion (IL)

(73) Assignee: Applied Materials South East Asia Pte. Ltd., Singapore (SG)

(*) Notice: Subject to any disclaimer, the term of this patent is extended or adjusted under 35 U.S.C. 154(b) by 1211 days.

(21) Appl. No.: 11/781,454

(22) Filed: Jul. 23, 2007

(65) Prior Publication Data
US 2009/0030630 A1     Jan. 29, 2009

(51) Int. Cl.
*G01N 21/00*    (2006.01)
(52) U.S. Cl. ................................. 356/237.2
(58) Field of Classification Search .......... None
See application file for complete search history.

(56) References Cited

U.S. PATENT DOCUMENTS

| | | |
|---|---|---|
| 4,926,489 A | 5/1990 | Danielson et al. |
| 5,699,447 A | 12/1997 | Alumot et al. |
| 6,590,198 B1 | 7/2003 | Zarnowski et al. |
| 2003/0123055 A1 | 7/2003 | Jaeschke |
| 2004/0146295 A1 | 7/2004 | Furman et al. |
| 2008/0037933 A1 | 2/2008 | Furman et al. |

FOREIGN PATENT DOCUMENTS
EP      0819933 A2    1/1998

OTHER PUBLICATIONS

Negevtech Ltd., EP Application No. 0825419.0, EP Search Report dated Mar. 13, 2009, 3pp.
Negevtech Ltd., EP Application No. 0825419.0, EP Search Opinion dated Mar. 23, 2009, 5pp.

*Primary Examiner* — Gregory J Toatley
*Assistant Examiner* — Juan D Valentin
(74) *Attorney, Agent, or Firm* — SNR Denton US LLP

(57) ABSTRACT

An optical inspection tool can feature a double-speed and other modes whereby the inspection rate is increased by using pixel binning. For instance, the tool may include an array of pixels provided by one or more detectors. Some or all of the pixels in one or more of the detectors may be binned according to inspection requirements. Based on the reduction in effective pixels due to the binning, in some embodiments, the rate of imaging and scanning rate of the wafer (or other object) can be increased. Different portions of the array may be binned differently to provide for increased throughput during inspections; for instance, the binning arrangement across an array can be correlated to the features that will be imaged using the array.

20 Claims, 7 Drawing Sheets

US 8,098,372 B2

OPTICAL INSPECTION TOOL FEATURING MULTIPLE SPEED MODES

FIELD OF THE INVENTION

The present invention relates generally to inspection of objects, for example, semiconductor wafers, using optical inspection tools.

BACKGROUND

Inspection of semiconductor wafers (and other objects, such as reticles, flat-panel displays, photomasks, and the like) often involves scanning the wafer or other object to determine the presence or absence of defects. Generally speaking, when the inspection aims to detect miniature defects, the image of the wafer is obtained using high magnification, often the highest magnification available using the tool. However, the higher magnification also results in a slower inspection. In other contexts, lower magnification may be used. For instance, in dark-field inspection of a memory area, the area may be blank or nearly blank if, for example, if Fourier filtering is used in a manner sufficient to eliminate the repetitive features of the area. In such circumstances, detection of a defect can be less dependent on high resolution. As another example, many defect types of high interest may be quite large (relative to the smallest possible defect) and thus may be detected using low magnification. However, low magnification may not always be ideal.

SUMMARY

Disadvantages that may be encountered when using low magnification optics in an inspection tool can be avoided in some instances through the use of pixel binning at one or more detectors used for obtaining images in the optical inspection tool. For instance, the numerical aperture of the lower magnification lenses is typically smaller than the numerical aperture for the high magnification lenses and thus less light is collected for imaging. Less light can degrade the quality of images, and lower-quality images can adversely affect defect detection.

By binning pixels, the optical components with the highest magnification can be used to image an area at a lower resolution. In some embodiments, pixel binning allows for the tool to produce an image output at an increased rate, so the advantageous numerical aperture of the high-magnification optics can be utilized without the loss in speed due to processing time for the high resolution images that would be obtained in the absence of binning. Of course, binning can be used in conjunction with any optical magnification of the tool, and is not limited to only the highest or any other particular magnification. Additionally, by binning pixels, the signal to noise ratio for the detector may advantageously be increased; such an increase would be absent for low magnification inspections using un-binned pixels.

In some embodiments, binning can be combined with an increase in the apparent rate of motion between the imaging components and the wafer and increases in the illumination pulse rate (if pulsed illumination is used) to increase the speed of inspections. For example, by binning pairs of pixels into a single pixel (such as combining two rows into a single row), the tool can be configured to image a wafer at a doubled rate of speed. However, as will be noted below, any suitable multiplication can be achieved using any suitable binning methodology or methodologies. In some embodiments, mixed binning may be used wherein pixels of an array may be binned in different ways across the array and/or within a single detector.

BRIEF DESCRIPTION OF THE SEVERAL VIEWS OF THE DRAWINGS

A full and enabling disclosure including the best mode of practicing the appended claims and directed to one of ordinary skill in the art is set forth more particularly in the remainder of the specification. The specification makes reference to the appended figures, in which:

Use of like reference numerals in different features is intended to illustrate like or analogous components.

DETAILED DESCRIPTION OF THE PREFERRED EMBODIMENTS

Figure 1:
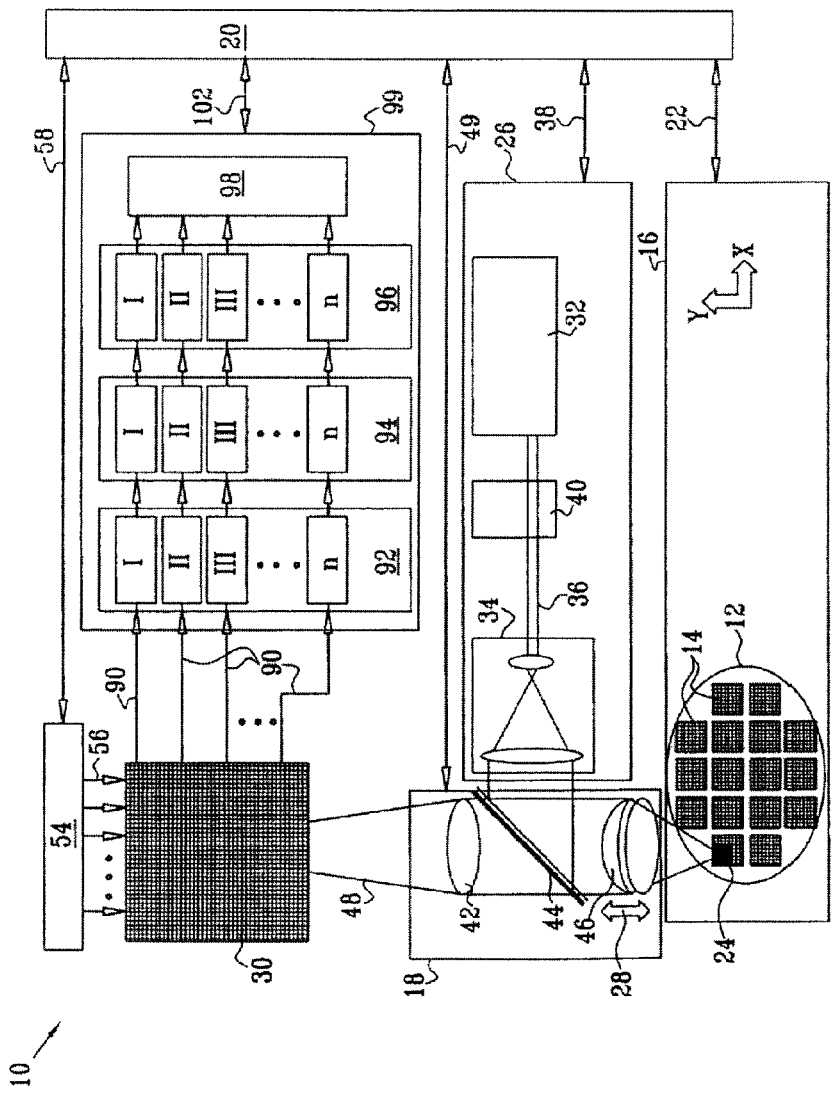
FIG. 1 is a block diagram of components in an exemplary optical inspection system.

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the present disclosure includes modifications and variations as come within the scope of the appended claims and their equivalents.

An optical inspection system can include a pulsed illumination source, an imager comprising an array of binnable pixel elements, and a control system configured to provide at least one motion control signal to at least one other component of the inspection system that varies what is in view of the array. Some or all of the pixels of the array may be binnable. Specifically, the imager can comprise one or more detectors, with the pixels from the detector(s) forming the array. In some embodiments, the pixels may be selectively binned by sending control signals to the detector(s) to configure whether and/or how the pixels are binned, while in other embodiments, the binning may be a fixed feature of the detector(s).

For example, the optical inspection system can be configured to image a plurality of areas, such as frames, of the object along an inspection path by changing which area of the object is in view of the array. The change in view can occur at a rate of motion. For instance, the rate of motion may correspond to an apparent rate of motion due to changing the view by moving optical components, such as lenses or rotating mirrors. As another example, the rate of motion may correspond to the rate at which the object is moved or relative motion is otherwise imparted between the object and the array.

In some embodiments, the inspection system can be configured to change the binning arrangement in real time, such as in between imaging frames (or other areas). For example, the different binning arrangements can be based on data included in the inspection recipe setup. The binning arrangements can be determined manually and/or automatically, for instance, by associating areas of a wafer (or other object) with certain types of binning.

In some embodiments, the inspection system can be configured to selectively operate in one of a plurality of N-speed modes, including at least a base mode where N equals one and one or more other modes where N is greater than one. For instance, in some embodiments, the tool can operate in a double-speed mode where N equals two. Multiple different N-multiplied speed modes can be selected in some tools.

In a base speed mode, the control system can provide one or more signals to change the area in view of the array at a first rate of motion, the pulsed illumination source can be configured to provide illumination at a first pulse rate, and the system can be configured to image an area using a first number of pixels. For instance, the pulse or other illumination apparatus, the component or components used to change the view of the imager, and the imaging apparatus may be synchronized so that an area is illuminated and imaged and, in the interval following imaging, the next area is brought into view. In an N-multiplied speed mode, the detector can be configured to bin at least some pixel elements so that the system images an area using a second number of pixels. The second number of pixels is about equal to the first number of pixels divided by a multiplier N. The number of pixels may or may not be exactly equal due to the particular binning scheme that is used. Further, in the N-multiplied speed mode, the illumination source can be configured to provide illumination at a second pulse rate, the second pulse rate being equal or about equal to the first pulse rate multiplied by N.

In some embodiments, in an N-multiplied speed mode, the control system provides signals to change the area in view of the imager at a second rate of motion, the second rate of motion being about equal to the first rate of motion multiplied by N. In some embodiments, binning comprises configuring the detector(s) to average N adjacent detector rows to a single row. In some embodiments, binning comprises configuring the detector(s) to average N adjacent detector columns to a single column. Furthermore, in some embodiments, 2-D binning is used in at least one N-speed mode, where pixels in L adjacent rows and M adjacent columns are averaged into a single pixel, with L*M being about equal to N.

In some embodiments, the inspection system can further comprise an image analysis system configured to evaluate the images using any suitable technique or techniques and to determine the presence or absence of a defect (or potential defect). For example, images may be compared to one another, to one or more references, and/or may be analyzed for features or characteristics that could indicate a defect. In at least one N-multiplied speed mode, the control system can be configured to change the view of the array at a rate less than the first rate of motion multiplied by N so that at least some areas are imaged more than once. For instance, if frames are used, an area may be imaged by overlapping frames. Determining the presence or absence of a defect (or potential defect) can be based at least in part on whether the defect lies in an area of the object imaged by overlapping frames.

An optical inspection system can comprise an imager comprising an array of binned and/or binnable pixel elements, with the array provided using at least one detector that is included in the imager. For example, one or more detectors may be physically and/or optically positioned to form a continuous array of pixels to receive an image of a frame of a wafer undergoing inspection. The inspection system can be configured to bin at least some pixels in the array differently than other pixels in the array. For instance, in at least one single detector, some pixels may be binned while other pixels in the same detector are not binned at all, in some embodiments. In some embodiments, the array may comprise at least one detector where some pixels in the detector are binned in a first grouping while other pixels in the same detector are binned in a second grouping. For example, some pixels may be binned using row averaging while other pixels are binned using column averaging. In some embodiments, the array may comprise a plurality of detectors, with different binning between at least two of the detectors. For instance, one detector in the array may comprise binned pixels and at least one other detector in the array may comprise no binned pixels. In some embodiments, the optical inspection tool can be configured to change the binning of at least some pixels in the array during the inspection process. For example, the binning may change based on whether high-resolution imaging is needed for a particular area being inspected.

A method of optical inspection can comprise accessing data indicating a selection of an inspection mode from a plurality of N-speed inspection modes. For example, the data may be received from an operator, may be accessed from a file, such as an inspection recipe, and/or may be the result of an algorithm used to determine a speed mode for use in some or all of an inspection run.

The method can comprise changing which area of an object is in view of an imager, the imager comprising at least one detector, with changing occurring at a rate of motion. For example, the view can be changed by imparting relative motion by moving the object on a translational stage relative to a non-moving imager. Alternatively or additionally, the imager may move. As another example, apparent motion may be imparted, wherein the object may remain stationary while the view of the imager is changed by optical components, such as a rotating mirror or other component(s), or by moving the imager. The method can further include illuminating the object with pulsed illumination at a pulse rate and imaging a plurality of frames at an imaging rate, each frame comprising a number of pixels. The pulse rate and the imaging rate can comprise a base pulse rate multiplied by N and a base imaging rate multiplied by N. The number of pixels can be about equal to the effective base number of pixels divided by N, with the number of pixels achieved through pixel binning at the at least one detector. In some embodiments, the method can comprise imparting relative motion at a rate about equal to a base rate multiplied by N. N may be any suitable number, and in some embodiments is equal to or about equal to one (the base speed), two, three, four, or any other suitable number.

In some embodiments, the method can comprise selecting the number of pixels for imaging by binning pixels, such as by averaging N adjacent detector rows to a single row in at least one detector and/or averaging N adjacent detector columns to a single column in at least one detector. In some embodiments where N is greater than 1, the method can comprise changing the view of the imager a rate grater than the base rate, but less than the base rate multiplied by N and evaluating imaged frames to determine the presence or absence of a potential defect, with determining being based at least on whether the potential defect was in an area imaged by overlapping frames. Thus, in some embodiments, a tool can support multiple N-speed inspection modes where N is the same but the rate of relative or apparent motion differs. In some embodiments, an N-speed inspection mode can be selected as part of an ongoing inspection to change the mode from a first N-speed inspection mode to a second N-speed inspection mode.

A method of inspecting an object can comprise binning an array of pixels, with the pixels provided as part of an imager comprising at least one detector, and imaging at least a portion of an object using the array of binned pixels. At least some pixels in the array can be binned differently than other pixels in the array. In some embodiments, all of the pixels in the array may be binned, while in other embodiments, some pixels are binned and some pixels are not binned. In some embodiments, binning can comprise binning some pixels in the detector and not binning some pixels in the same detector. In embodiments where the array comprises multiple detectors, binning can comprise binning some pixels in one detector differently from the pixels in at least one other detector. For instance, pixels in at least one detector may not be binned at all. The method can comprise imaging at least a first and a second portion of the object using the array, and the method may further comprise sending a signal to change the binning of at least some of the pixels in the array between imaging the first and second portions.

In some embodiments, an optical inspection system can comprise an imager comprising an array of binnable pixel elements. In some embodiments, the imager can comprise pixels of at least time-delayed integration sensor. The time-delayed integration sensor can be a two-dimensional matrix (i.e. 2-D array) configured to provide a 1-dimensional output. The system can be configured to image a plurality of areas of the object as the area of the object in view of the array is changed. When time-delayed integration is used, illumination is not pulsed in some embodiments. The optical inspection system can be configured to selectively operate in at least a base speed mode and at least one N-multiplied speed mode. In the base speed mode, the system can be configured to change which area of the object is in view at a first rate of motion, and the system can be configured to image an area using a first number of pixels. In an N-multiplied speed mode, the at least one detector can be configured to bin at least some pixel elements so that the system images an area using a second number of pixels, with the second number of pixels is about equal to the first number of pixels divided by an integer N. The binning can be parallel to the direction of relative motion between the imager and the object, perpendicular to the direction of relative motion between the imager and the object, or both parallel and perpendicular.

A method of inspecting an object can comprise accessing data indicating a selection of an inspection speed mode from a set of N-speed modes, the set comprising a base speed wherein N=1 and at last one other speed wherein N is greater than 1. The method can further comprise changing which area of the object is in view of an imager, the imager comprising at least one time-delayed integration sensor; and imaging a plurality of areas of the object, each area comprising a number of pixels. The number of pixels may be about equal to a base number of pixels divided by N. The time-delayed integration sensor can comprise a two-dimensional sensor configured to provide one-dimensional output as the view of the object changes due to relative or apparent motion. The output may be provided by a tool that can selectively operate using time-delayed integration and other imaging techniques, such as instantaneous area scanning using pulsed illumination. However, in time-delayed integration mode, the tool does not necessarily use pulsed illumination. Of course, other tools may operate only using time-delayed integration mode.

FIG. 1 is a block diagram showing components in an exemplary optical inspection tool. The present subject matter may be implemented by configuring any suitable inspection tool, and the tool briefly discussed below is for purposes of illustration only. For instance, the tool may comprise a Negevtech 3100 optical inspection tool (available from Negevtech, Ltd. of Rehovot, Israel) adapted to support pixel binning in accordance with one or more of the embodiments discussed herein. Discussion of exemplary embodiments of an inspection tool can be found in Negevtech U.S. patent application Ser. No. 10/345,097, filed Jan. 15, 2003, which is incorporated by reference herein in its entirety.

As shown in FIG. 1, a patterned semiconductor wafer 12 featuring a plurality of wafer dies 14, is placed and aligned on a continuous moving XY translation stage 16 to impart motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging system 18 in a serpentine pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution.

Figure 2:
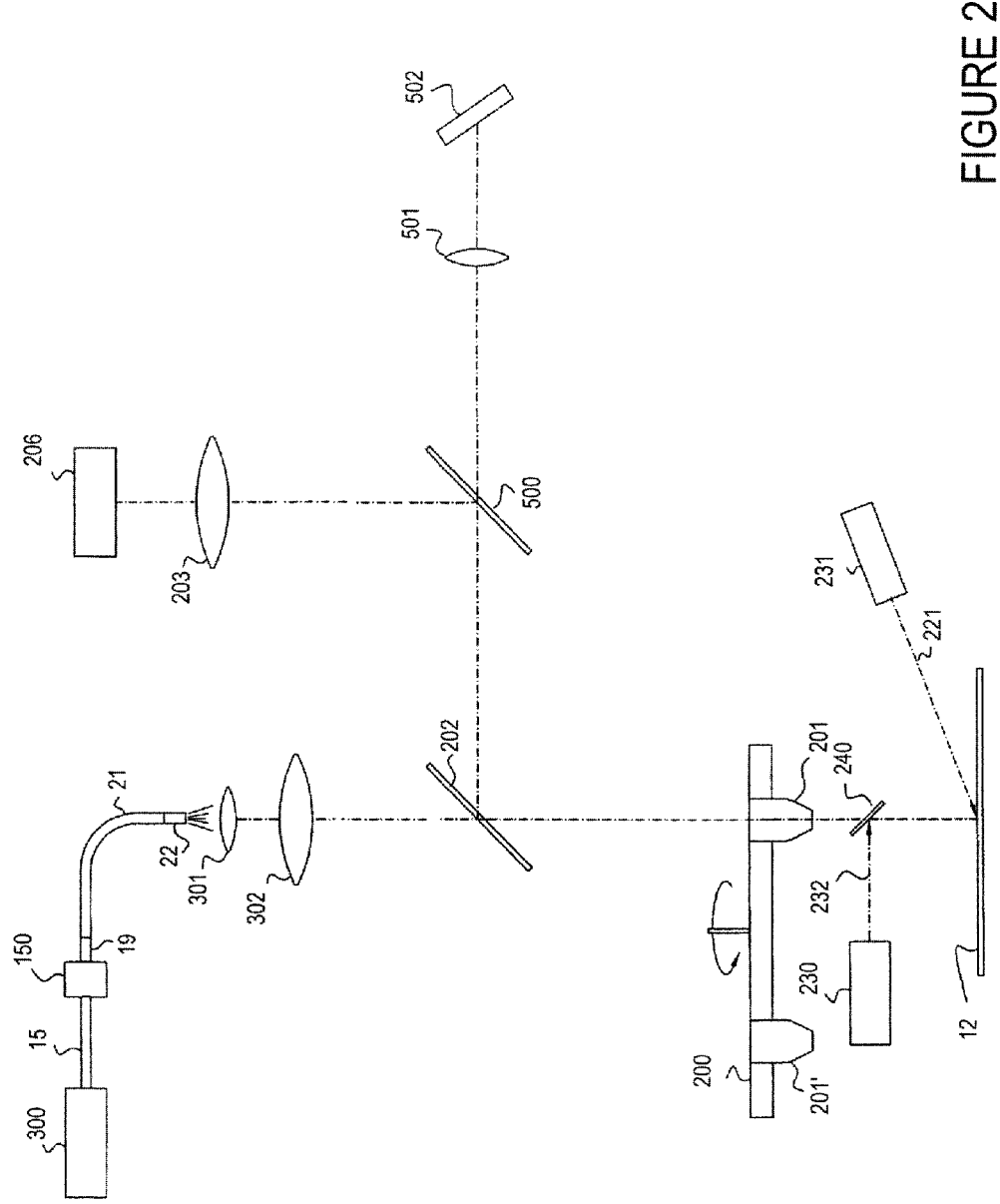
FIG. 2 is a block diagram illustrating illumination and detection components in an exemplary optical inspection system.

An illumination system 26 is provided, and can include a repetitively pulsed laser 32, a laser beam expander 34, a laser beam light path 36, and control/data links 38 as shown in FIG. 2. Regardless of the type of illumination, pulsed illumination enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. Although in these examples a pulsed illumination source is used, one or more continuous sources may be used as discussed later in the specification.

In system 10, pulse rate, i.e., pulses per second, of pulsed laser 32 can be synchronized with frame speed of the array of individual matrix photo-detectors of focal plane assembly 30. A laser pulse, illuminating field of view 24 of a wafer die 14 for a time duration of microseconds to nanoseconds (compared to milliseconds frame time of temporally gated camera system focal plane assembly 30 of matrix photo-detectors), results in instantaneous illumination of field of view 24 of an inspected wafer die 14. In one very short laser pulse, a relatively large number of pixels, for example, about forty eight million pixels, of focal plane assembly array 30 can be simultaneously illuminated, and there is essentially no relative movement among the pixels. The laser light pulse duration is preferably shorter than the image pixel dwell time or about the same order of magnitude to the pixel dwell time, where the pixel dwell time refers to the time a point on the wafer is imaged by a detector pixel while the wafer is moving.

The pulse and imaging rate can depend on the speed at which a tool comprising multiple speed modes is operating and/or may otherwise be interrelated to the characteristics/arrangement of pixel binning in the array. Generally speaking, a tool that supports multiple speed modes can change the rate at which frames or other areas are imaged. The control system (such as control system 20) may comprise one or more suitable devices or circuits that provide one or more control signals to other components that vary what is in view of the array and provide for imaging.

For instance, in the examples above, the stage components (e.g. servo motors) vary what is in view of the array by moving the wafer. In other embodiments, though, the view of the array can be varied by other components, such as by changing the position of one or more components, such as a rotating (or otherwise moving) mirror. As another example, the view of the array can be changed by varying the position of the imager. Regardless of how the area of the object in view of the array is changed, the tool can support different rates of motion. For instance, if an N-multiplied speed mode is selected, the area of the wafer that is in view of the array may be changed at a faster rate of motion by increasing the stage velocity. As another example, if a rotating mirror or other component(s) are used, those components may be moved faster in one or more N-multiplied speed modes.

Similarly, in one or more N-multiplied speed modes, the frame and pulse rate can be increased by sending one or more control signals to the imager and illumination components. However, other embodiments may not utilize pulsed illumination. For example, if the imager array comprises one or more time delayed integration (TDI) sensors, continuous illumination may be provided. In an N-multiplied speed mode, the signal transfer rate for the TDI sensor(s) can be synchronized with the rate at which the view of the array is changed.

The control signal(s) that are provided can be in any suitable form, and the form of the signal(s) is not essential to the present subject matter. For instance, the control signal(s) may comprise data signals (e.g. commands) that are further processed by the component(s) that receive the commands. As another example, the control signal(s) may comprise electrical or mechanical signals that cause the other components to operate as desired. Similarly, the particular arrangement of control system 20 is not essential. For example, control system 20 can comprise any suitable computing device, such as general purpose computer, another computing device (e.g. microcontroller or other processing hardware), analog, and/or digital circuitry that provides suitable control signals.

Returning to FIG. 1, an optical imaging system can include a focusing lens 42, a beam splitter 44, an objective lens 46, and control/data links 49. This system is suitable for ultra fast high resolution synchronous imaging of high magnification, for example, 50× of wide field of view 24 of one or more wafer die(s) 14. An automatic focusing system 28, including sensor and control devices (not shown) can be provided which, via optical imaging system 18, automatically maintains wafer 12, and therefore, wafer die(s) 14, in focus. An automatic focusing system, such as system 28, automatically adjusts and sets the position of objective lens 46 of optical imaging system 18 for optimum focus of all wafer dies 14 on wafer 12. Optical imaging system 18 is in communication with the central control system 20 via control/data links 49. During operation of wafer inspection system 10, focusing lens 42 images laser light 48, where laser light 48 represents light reflected, scattered and diffracted by wafer 12, onto focal plane assembly 30. However, the particular arrangement of the auto-focusing system can vary and is not essential to the present subject matter.

Focal plane assembly 30 can include one or more detector ensembles arranged to provide an array of pixel elements. Each detector ensemble can feature a single or multiple two-dimensional matrix photo-detectors. For example, in some embodiments assembly 30 comprises at least one two-dimensional CCD matrix photo-detector, focal plane assembly electronics 54, and control/data links 56, 58, and 90, enabling high capacity and ultra fast high resolution synchronous imaging of a wafer die 14. Focal plane assembly 30 is in communication with central control system 20 via control/data links 56 and 58. At least one detector in focal plane assembly can be configured to bin at least some of the pixel elements in the detector. The detector may have a fixed (i.e. unchangeable) binning or binning may be selectable. For instance, the detector may be toggled between a fixed binning and no binning. As another example, the detector may be configured to bin one or more groups of pixels in different ways according to selection systems. Any suitable implementation can be used to accomplish binning. For instance, pixels may be binned by averaging the charge value for the binned pixels at the detector.

In some embodiments, the binning of the pixels may be changed in real time, such as changing the binning arrangement in between imaging frames or other areas. For example, an inspection recipe may specify different binning arrangements and/or types of binning for different frames. The recipe may specify such arrangements/types based on manual and/or automatic analysis of wafer features and other considerations.

Reference is now made to FIG. 2, which is an overall schematic side view of components in an illumination system of the defect detection apparatus, according to an exemplary embodiment of the present subject matter. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 2 shows a bright field illuminating laser source 300 delivering its output beam 15 into an optical delivery fiber bundle 21, preferably by means of a laser to fiber coupler 150. This optical fiber bundle 21 provides both uniform illumination on the sample and coherence breaking of the laser illumination. In some embodiments, only a single fiber bundle is used, but it is to be understood that a serial fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006, and incorporated by reference herein for all purposes.

From the output termination of the fiber bundle 21, the laser beam is imaged by means of illumination transfer lenses 301, 302 onto the objective lens in use 201, which is operative to focus the illumination onto a wafer 12 being inspected. Appropriate alternative objective lenses 201' can be swung into place on an objective revolver 200, as is known in the microscope arts. The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector or detectors of the imager, with the detector(s) represented in FIG. 2 at 206. The second beam splitter 500 is used to separate the light going to the imaging functionality from the light used in the auto-focus functionality, which is directed by means of the auto-focus imaging lens 501 to the auto-focus detector 502.

When conventional dark field illumination is required for the imaging in hand, a dark field side illumination source 231 is used to project the required illumination beam 221 onto the wafer 12. When orthogonal dark field, or obscured reflectance dark field illumination is required for the imaging in hand, an alternative dark field illumination source 230 is used to project the required illumination beam 232 via the obscured reflectance mirror 240 onto the wafer 12 orthogonally from above. FIG. 2 indicates sources 300, 231, and 230 at different locations. However, any or all of sources 300, 230, and 231 may comprise the same light source, with the bright field, dark field, and obscured reflectance dark field effects achieved through moving the source(s) and/or redirecting illumination to the appropriate angle using one or more optical components.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. As another example, the tool may be connected to suitable hardware, or image data may be provided to suitable hardware in any other manner.

As an example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

As noted above, however, the full resolution of the inspection tool may not always be required depending, for example, on the nature of the area of the object being inspected and/or the requirements of a particular defect determination technique. For example, as was noted above, a tool may operate in dark-field inspection mode, such as when inspecting memory areas of a wafer or die. The use of Fourier filtering may advantageously increase the probability of detecting a defect in an area by filtering out repetitive patterns in the area so that any defect will stand out. Therefore, lower resolution may be used for such an inspection. Similarly, many defects of great importance may be large enough to stand out at relatively low magnification/resolution. Therefore, in embodiments of the present subject matter, some of the pixels that are used to obtain inspection images may be binned.

Binning can be achieved in any suitable way. For instance, pixels may be binned in software, hardware, or using both software and hardware. However, hardware-based binning, especially binning at the detector, may be advantageous in some embodiments. Consider the following example of the effect of binning on two different defects, with sizes of 1 pixel and 2 pixels, respectively. In the examples below, the defect signal is symbolized as 'S', the noise of the camera electronics in $n_e$ and the other noise is indicated as $n_w$. For instance, in most situations, the other noise $n_w$ mainly originates from the wafer surface roughness. The total noise (expressed as a power signal) is therefore $\sqrt{n_e^2 + n_w^2}$ For a single pixel defect, the signal to noise ratio is:

$$S/\sqrt{n_e^2 + n_2^2} \tag{Eq. 1}$$

If the defect is located in a pixel that is binned (1:2) in image processing, the signal to noise ratio is reduced by factor of $\sqrt{2}$, since the signal remains and the noise from two pixels is added (root sum square addition):

$$S/\sqrt{2n_e^2 + 2n_w^2} \tag{Eq. 2}$$

When the binning is carried out in the detector electronics, the electronic noise only occurs once, since a single signal from both pixels is provided after binning. Therefore, the signal to noise ratio for two pixels binned at the detector is:

$$S/\sqrt{n_e^2 + 2n_w^2} \tag{Eq. 3}$$

This signal to noise ratio is less than the no-binning case, but a double-speed inspection rate is possible. When the noise from sources other than electronics is not significant (i.e. as $n_w$ tends toward zero), the signal to noise ratio for binning at the detector electronics is about the same as the no-binning case. It is also clear that the electronic binning is better than the image processing binning.

In non-miniature defects, for example, with size of 2 pixels, the signal to noise ratio of the non-binning case is same as for single pixel defects:

$$S/\sqrt{n_e^2 + n_w^2} \tag{Eq. 4}$$

In image processing binning the signal to noise ratio is as follows:

$$2S/\sqrt{2n_e^2 + 2n_w^2} = \frac{S}{\sqrt{\frac{n_e^2}{2} + \frac{n_w^2}{2}}} \tag{Eq. 5}$$

If binning is performed in detector electronics, though, the signal to noise ratio is the lowest:

$$2S/\sqrt{n_e^2 + 2n_w^2} = \frac{S}{\sqrt{\frac{n_e^2}{4} + \frac{n_w^2}{2}}} \tag{Eq. 6}$$

Based on the above, it is clear that binning at the detector can be more advantageous than binning in image processing. Additionally, although binning can introduce noise, the disadvantages of the increased noise can be offset by efficiency gains from higher speeds that are possible with binning. Of course, in some embodiments, it is possible to conduct inspections where pixels are binned while the pulse rate, imaging rate, and/or the rate of motion remain at a base level.

As was mentioned above, in embodiments of inspection systems and methods that utilize pulsed illumination, the rate of motion, pulse rate, and/or imaging rate can be increased in some instances when binning is used. However, other embodiments of inspection systems and methods may not use pulsed illumination. For example, an inspection system may utilize continuous illumination, such as lamps or a continuously-illuminated laser. The system may be configured to always use continuous illumination or may selectively operate using continuous or pulsed illumination. In any event, binning may be used in conjunction with any illumination, including, but not limited to, pulsed and continuous illumination.

For example, an inspection system may utilize continuous illumination in performing inspections using a time delayed integration sensor. For instance, one or more sensors may be used to provide an integrated exposure where the change of what is in view of the array is synchronized with signal charge transfer timing for enhanced sensitivity. For example, an array comprising one or more CCD, CMOS, and/or other sensors may be used. Depending on the required resolution, pixels may be binned either parallel to the direction of scanning, perpendicular to the direction of scanning, or both parallel and perpendicular to the direction of scanning. In such embodiments, since the illumination is continuous, the pulse rate need not be varied in an N-speed mode (and no pulses are necessary at all). Instead, the rate of motion at which the sensor(s) view of the wafer changes (e.g. stage rate, mirror or other component rotational velocity, etc.) can be increased based on the binning. The signal transfer speed of the TDI sensor(s) can be appropriately synchronized to the rate of motion at which the view of the array is changed.

Several examples of binning arrangements will now be discussed. It is to be appreciated that the particular implementation of binning itself may be achieved in any suitable way. Additionally, the particular examples of binning arrangements are intended for teaching and illustration only and are not intended to be limiting.

Figure 3:
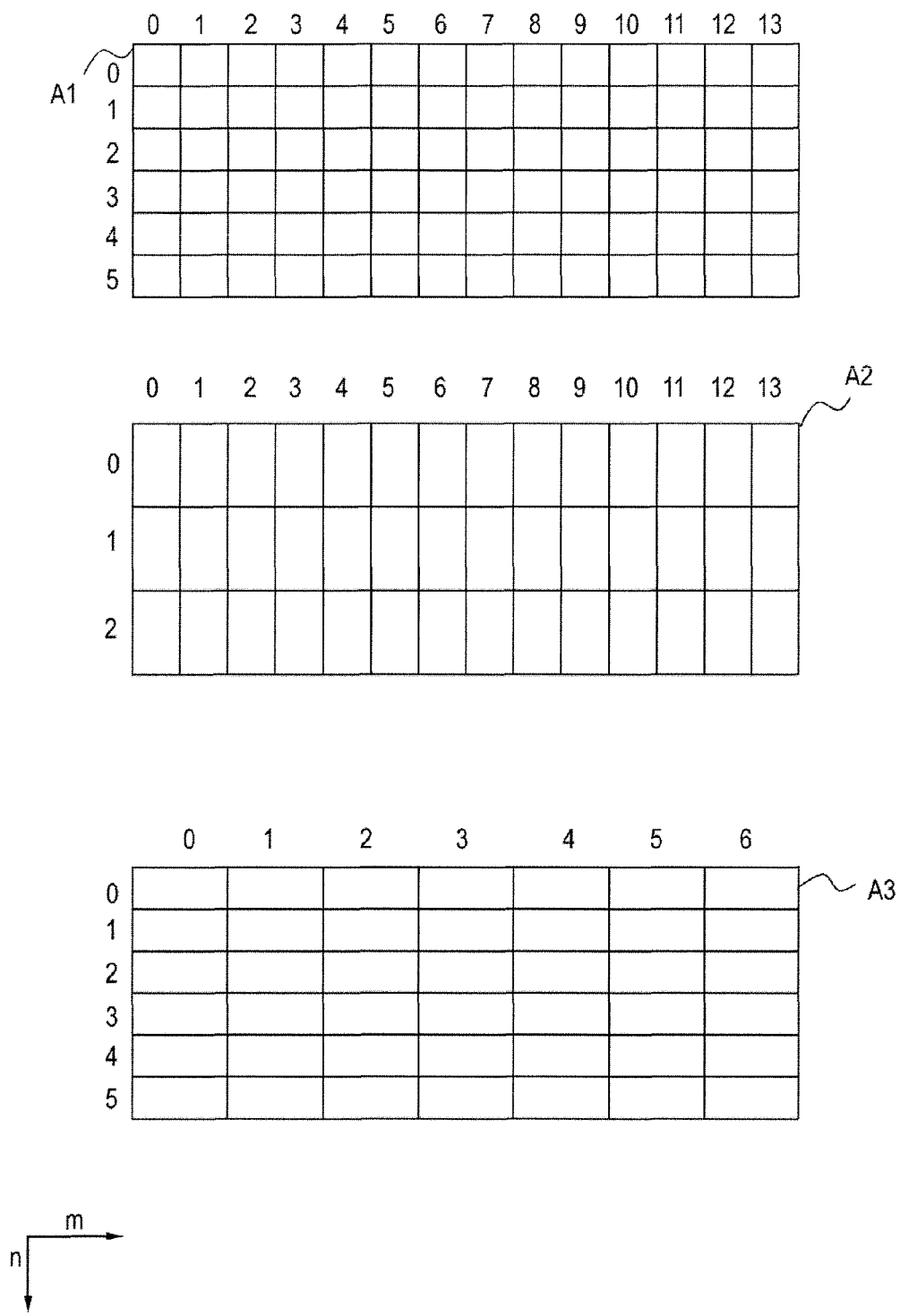
FIGS. 3, 4, and 5 are each diagrams depicting exemplary arrays of pixels.

FIG. 3 is a diagram showing three exemplary pixel arrays A1, A2, and A3. Generally, in the present specification, pixels (binned or otherwise) will be identified as an address (m,n), where m is a column address and n is a row address. Address (m,n) in this specification is relative to the pixel in the upper left hand corner of the array, which is (0,0). Additionally, each array may comprise pixels from a single detector or pixels from multiple detectors. In array A1, no pixels are binned. However, Array A2 shows the results when the A1 pixels have been binned using row binning. In this example, 1:2 row binning is shown, and the pixels in adjacent rows 0 and 1, 2 and 3, and 4 and 5 of array A1 have been binned. Pixel (0,0) in array A2 comprises pixels (0,0) and (0,1) shown in array A1, pixel (1,1) in array A2 comprises pixels (1,2) and (1,3) of A1, and so on.

Binning may be achieved in any suitable way. For instance, binning of pixels (0,0) and (1,0) may be implemented by averaging the charge from pixel (0,0) and (1,0) at the detector. Array A3 shows a different type of binning, namely the results of binning pairs of adjacent columns of array A1. For instance, pixel (0,0) shown in array A3 may comprise the average of pixels (0,0) and (1,0) shown in array A1, and so on. In array A2, the number of effective pixels is forty-two, which is half of the effective pixels shown in A1. In array A3, the number of pixels is also forty-two, which is equal to half the effective pixels shown in A1.

Figure 4:
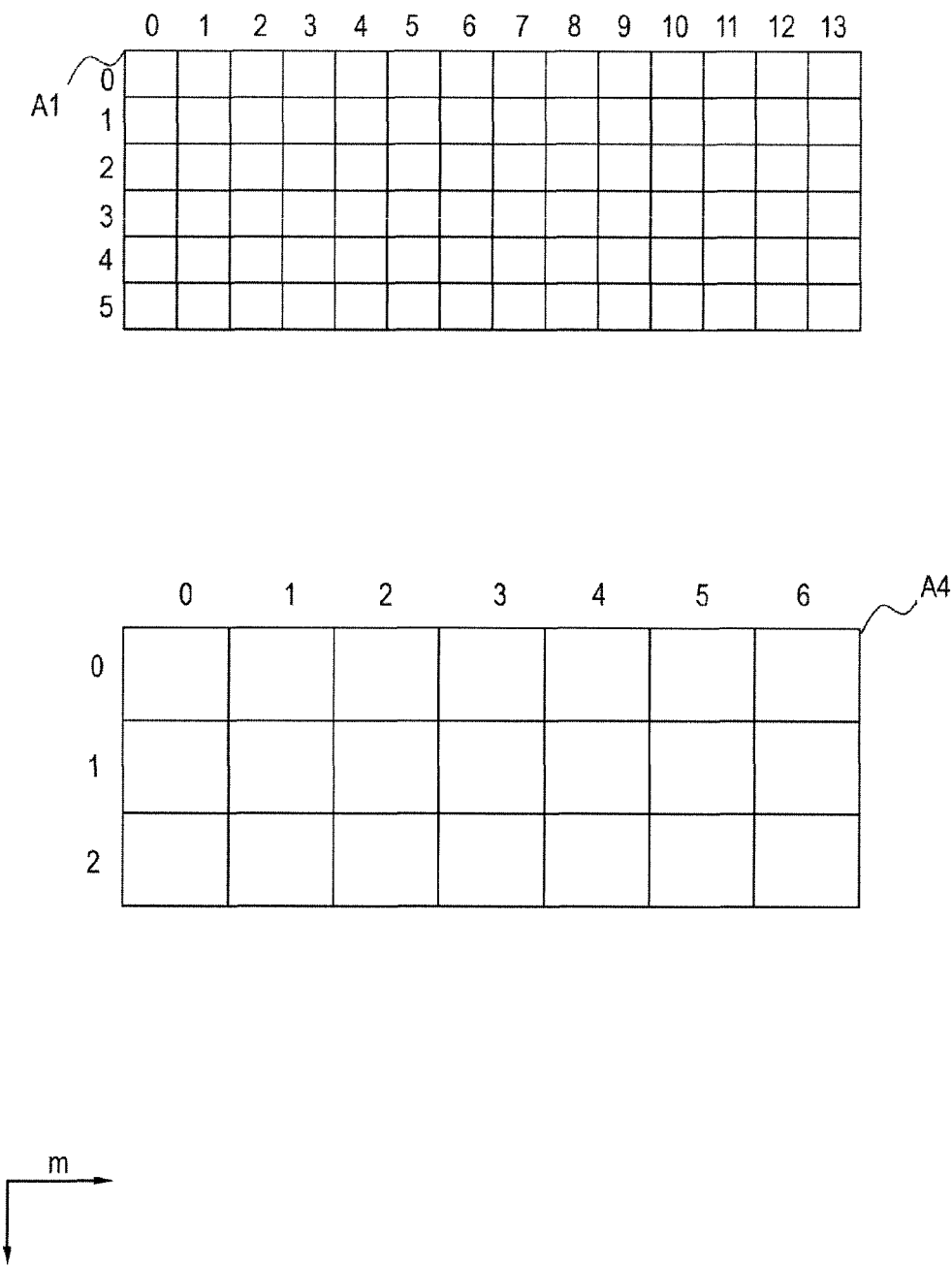

FIG. 4 illustrates pixel arrays A1 and A4. In array A4, pixels from rows and columns of array A1 have been binned. For example, pixel (0,0) of array A4 can comprise binning of pixels (0,0), (0,1), (1,0), and (1,1) shown in A1. In A4, the eighty-four effective pixels of A1 has been cut to twenty-one, which is one fourth of the effective pixels of A1.

Regardless of the particular binning technique or arrangement, the use of binning can be used to increase tool throughput in some embodiments. For example, during inspection, binning such as shown in FIG. 3 can be used to provide a tool having a single-speed mode using a first number of pixels with no binning (e.g. using array A0) and a double-speed mode where the number of pixels imaged by the tool is about equal to the number of pixels imaged in single speed mode divided by two (e.g. using array A1 or A2). Because of the reduced number of pixels that are imaged, the resources of the tool (such as memory, bandwidth, and the like) are effectively increased, in this example, by a factor of about two. Therefore, the rate of inspection can be increased by approximately the same factor without taxing the tool resources.

For instance, the rate of motion at which the tool changes the view of the imager array can be varied. For instance, the rate of motion of one or more components that vary what is in view of the array, the imaging rate, and the pulse rate can be doubled so that twice as many frames are illuminated and imaged in the same time interval over which a single frame is imaged in single-speed mode. However, other multiplication can be used. For instance, if the effective pixels are reduced by a factor of about three, then the movement rate, imaging rate, and pulse rate can be increased by a factor of about three (triple speed mode), and so on.

Generally speaking, in an N-speed mode, N is about equal to the effective base number of pixels (i.e. number of pixels without binning) divided by the effective number of pixels when binned for the N-speed mode. The term "about equal to" is meant to include situations where the numbers are exactly equal and also when the numbers are approximately equal. For instance, in certain binning arrangements, the ratio of pre-binning and post-binning pixels may not always be an integer. Nonetheless, the ratio is "about equal to" the closest integer.

In some embodiments, it may be advantageous to bin pixels and increase the illumination and frame rate but to not increase the rate of motion up to the full multiplied rate. For instance, the tool can be operated in double-speed mode, but the stage or other components may be configured so that the area in view of the array changes at a rate of motion less than about twice the single-speed rate. As another example, the binning may be four-to-one (quadruple speed mode) but the rate of motion may only be doubled. This will result in at least some areas of the wafer being imaged more than once. For instance, if frames are used, some areas may be imaged by overlapping frames. During the defect detection and/or evaluation process, the data regarding frame or other imaging overlap can be used to confirm, reject, or otherwise adjust the inspection results. For instance, the tool may be configured to flag or announce the existence of a defect (or a potential defect) in an overlapped area only if the defect is detected twice to avoid false alarms due to noise or other factors that would only be likely to trigger a detection once. As another example, to increase the probability of detecting a weak defect, a defect may be announced if it is detected once in an overlapped area.

Figure 5:
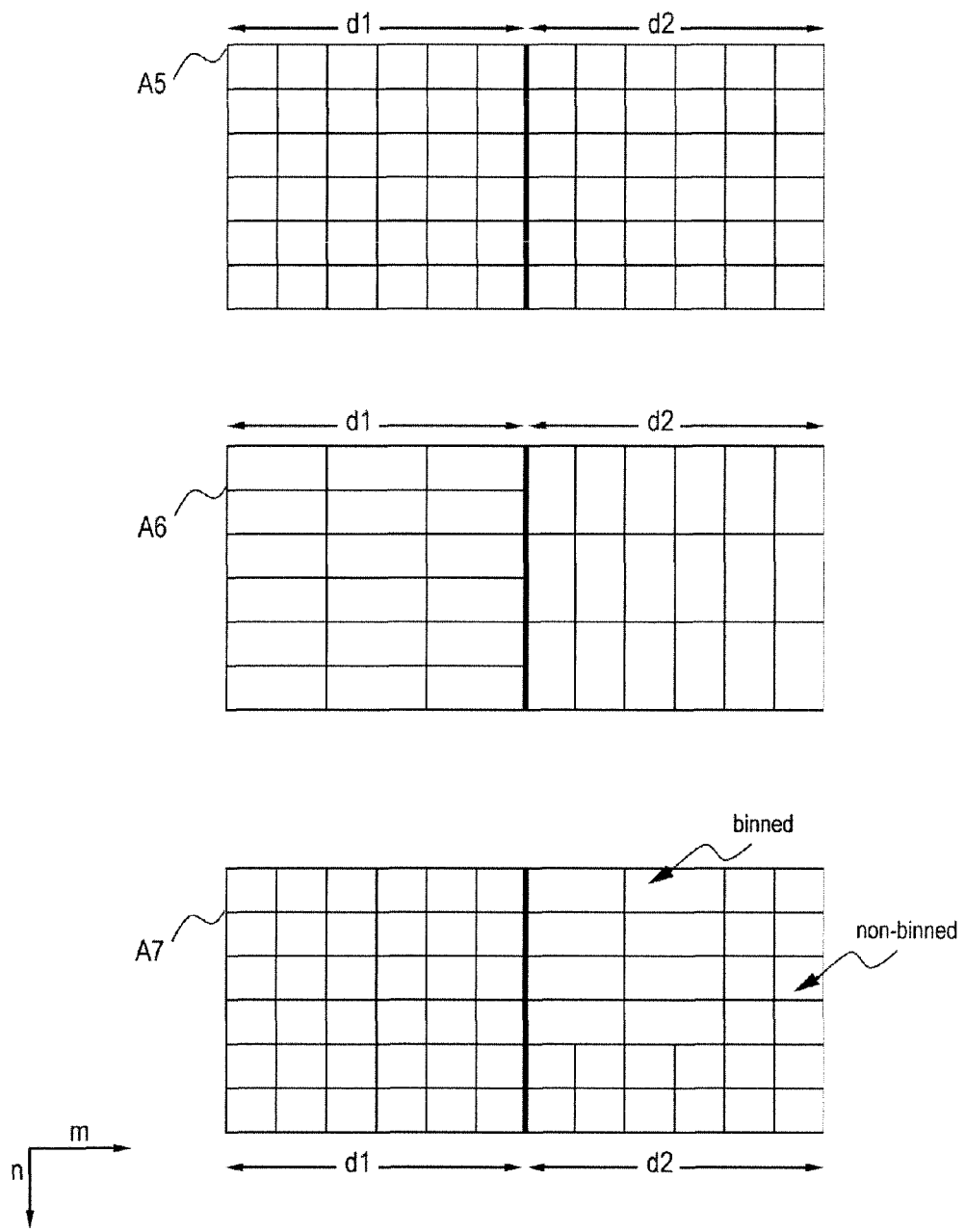

FIG. 5 is a diagram depicting three arrays A5, A6, and A7 which each comprise two adjacent detectors, d1 and d2. Array A5 shows d1 and d2 with no pixels binned. Each detector in this example comprises thirty-six pixels. In array A6, pixels of array A5 have been binned, but are binned differently between detectors d1 and d2. In this example, all pixels of d1 have been binned using binning of adjacent columns, while in d2 all pixels have been binned busing binning of adjacent rows. The effective pixels of array A5 is reduced by a factor of two, from seventy-two to thirty-six. In array A7, the detectors are binned differently, but in this example, one detector of the array (d1) is not binned at all. Array A7 also illustrates another exemplary binning implementation. In this example, part of detector d2 is binned differently from another part of the same detector. In this example, the labeled area is binned using column binning while the rest of d2 is not binned at all. Of course, a detector could include multiple types of different binning in combination with one another and/or no binning. Additionally, although in this example d2 is part of an array provided by a pair of detectors, the use of different binning within a detector need not be limited to any particular arrangement of detector(s) within an array.

Figure 6:
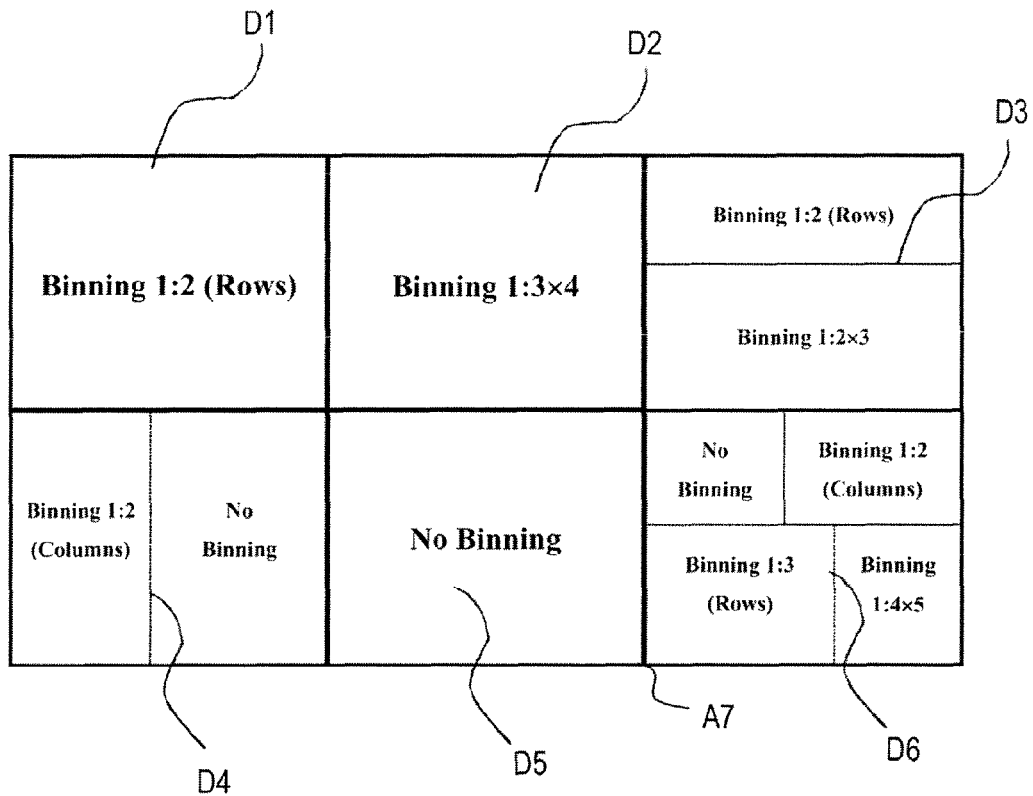
FIG. 6 is a diagram illustrating an example of a binning arrangement comprising several different types of binning within an array.

FIG. 6 illustrates an additional binning arrangement. In this example, the actual pixels are not shown, but instead the diagram shows a map of exemplary binning arrangements of pixels, with the binned areas including an indicator of the ratio 1:N. The pixels are comprised in six detectors arranged in an array A7, with the boundaries of the detectors indicated by the thick lines. As shown in FIG. 6, for detector D1, 1:2 row binning is used (i.e. pixels from pairs of adjacent rows are binned). For detector D2, 1:12 binning is achieved, with pixels from three adjacent rows and four adjacent columns binned together. Detector D3 is split: the upper portion uses 1:2 row binning and the lower portion uses 1:6 binning, with pixels from two adjacent rows and three adjacent columns binned. In detector D4, the left half is binned using 1:2 column binning and the right half is not binned. Detector D5 is not binned at all. Detector D6 is split four ways: the upper left-hand portion is not binned, the upper right-hand portion is binned using 1:2 column binning, the lower left-hand portion is binned using 1:3 row binning, and the lower right-hand portion is binned using 1:20 binning by binning pixels from four adjacent rows and five adjacent columns.

Mixed binning arrangements may be selected so that the resolution varies across the imaged area. For example, in some embodiments, the binning used in an inspection tool can be changed as the imaged frame changes. For instance, an area requiring high resolution may be imaged using non-binned pixels while an area requiring low resolution may be imaged using binned pixels. The tool may access data specifying which binning to use based on, for example, the relative location of the frame within the wafer, with the binning specifications generated as part of determining the inspection recipe. However, during the inspection process, certain of the frames may include areas that partially require high resolution and partially require low resolution. Thus, a mixed binning arrangement can be used for that area.

Figure 7:
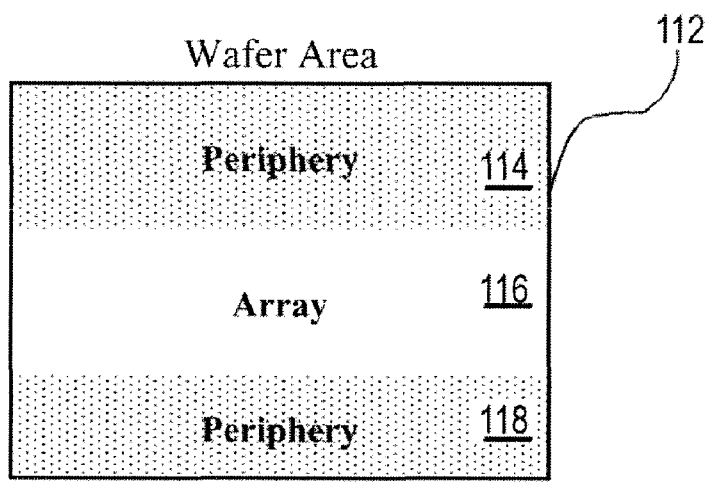
FIG. 7 is a diagram illustrating an example of an inspected area along with an exemplary binning arrangement comprising different types of binning within an array that correspond to different parts of the inspected area.
Figure 7:
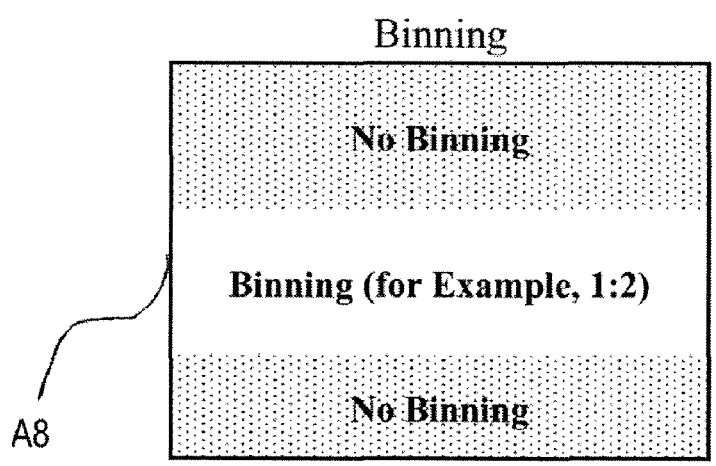

Turning to FIG. 7, an example of an area of a wafer 112 is shown along with a corresponding binning arrangement shown in array A8. For instance, area 112 may represent a frame or other portion of a wafer that is viewed by an inspection tool, with array A8 representing the binning arrangement of a pixel array (or portion of a pixel array) when area 112 is in view of the array (or portion of the array). In this example, the area 112 comprises a first periphery area 114, an array area 116 (such as, for example, an array of memory cells), and a second periphery area 118. As noted earlier in the specification, in some contexts, higher resolution may be desired for periphery areas 114 and 118 relative to area 116. This result can be achieved in this example by using the binning arrangement shown in array A8. The pixels in top and bottom portions of array A8 (corresponding to periphery areas 114 and 118) are not binned, while the pixels in the middle portion (corresponding to the inspected array area 116) are binned using 1:2 binning. Of course, any type and ratio of binning can be used, and this is provided for example only. Array A8 may be provided using a single detector or multiple detectors.

It is appreciated by persons skilled in the art that what has been particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed is:

1. An optical inspection system, the system comprising:
a pulsed illumination source;
an imager comprising an array of binnable pixel elements, the array comprising pixels of at least one detector;
a stage for supporting an object; and
a control system configured to provide at least one motion control signal to the stage that varies what area of the object is in view of the array;
wherein the optical inspection system is configured to image a plurality of areas of the object along an inspection path by changing, a rate of motion for the stage and thereby changing which area of the object is in view of the array;
wherein the optical inspection system is configured to operate in at least a base speed mode and at least one N-multiplied speed mode while inspecting the object during the same inspection, wherein the N-multiplied speed mode is a function of the base speed mode multiplied by an integer N;
wherein, in the base speed mode:
the optical inspection system is configured to change the area in view of the array by moving the stage at a first rate of motion,
the pulsed illumination source is configured to provide illumination at a first pulse rate, and
the system is configured to image a frame using a first number of pixels;
wherein, in the N-multiplied speed mode:
the optical inspection system is configured to change the area in view of the array by moving the stage at a second rate of motion, the second rate of motion about equal to the first rate of motion multiplied by the integer N;
the at least one detector is configured to bin at least some pixel elements so that the system images a frame using a second number of pixels,
wherein the second number of pixels is about equal to the first number of pixels divided by the integer N, and
the pulsed illumination source is configured to provide illumination at a second pulse rate about equal to the first pulse rate multiplied by the integer N.

2. The system as set forth in claim 1, wherein the detector is configured to bin at least some of the pixel elements by averaging at least two adjacent detector rows to a single row.

3. The system as set forth in claim 1, wherein the detector is configured to bin at least some of the pixel elements by averaging at least two adjacent detector columns to a single column.

4. The system as set forth in claim 1, wherein the detector is configured to bin at least some of the pixel elements in L adjacent rows and M adjacent columns, wherein L*M=the integer N.

5. The system as set forth in claim 1,
wherein the system further comprises an image analysis system configured to evaluate at least one of the imaged areas to determine the presence or absence of a defect;
wherein, in the N-multiplied speed mode, the area in view of the array is changed to a third rate of motion so that at least a portion of an area of the object is imaged more than once; and
wherein the evaluation is based at least in part on whether the defect lies in an area imaged more than once.

6. The system as set forth in claim 1, wherein the system is configured to selectively operate in at least a double-speed mode where the integer N equals two.

7. A method of inspecting an object, the method comprising:
   accessing data indicating a selection of an inspection speed mode from a set of N-speed modes, the set comprising a base speed and at least one N-speed, wherein the N-speed is equal to the base speed multiplied by an integer N and the integer N is greater than 1;
   changing, a rate of motion, of a stage supporting an object wherein an area of an object is in view of an imager, the imager comprising at least one detector;
   illuminating the object with pulsed illumination at a pulse rate based on the N-speed mode; and
   imaging a plurality of frames of the object at an imaging rate based on the N-speed mode, each frame comprising a number of pixels;
   wherein the number of pixels is about equal to a base number of pixels divided by the integer N, the pulse rate is about equal to a base pulse rate multiplied by the integer N, and the imaging rate is about equal to a base imaging rate multiplied by the integer N,
   wherein the base speed mode is adjusted during an inspection to change from a base speed mode to the at least one N-speed mode.

8. The method as set forth in claim 7, wherein the method comprises selecting the number of pixels for imaging by averaging at least two adjacent detector rows to a single row in at least one detector.

9. The method as set forth in claim 7, wherein the method comprises selecting the number of pixels for imaging by averaging at least two adjacent detector columns to a single column.

10. The method as set forth in claim 7, wherein the integer N is greater than one, and the method further comprises:
    changing which area of the object is in view of the imager at a rate of motion that is greater than the first rate of motion but less than the second rate of motion so that at least some imaged frames overlap in coverage of the object;
    comparing a plurality of imaged frames to one or more reference frames; and
    determining the presence or absence of a potential defect responsively to the comparison;
    wherein determining is based at least in part on whether the potential defect lies in an area of the object imaged by overlapping frames.

11. The method as set forth in claim 7, wherein the integer N is equal to about two.

12. The method as set forth in claim 7, wherein the N-speed mode is adjusted during an inspection to change from a first N-speed mode to a second N-speed mode during the inspection.

13. An optical inspection system, the system comprising:
    an imager comprising an array of binnable pixel elements, the array comprising pixels of a time-delayed integration sensor;
    a stage for supporting an object; and
    a control system configured to provide at least one motion control signal to the stage that varies what area of the object is in view of the array;
    wherein the optical inspection system is configured to image a plurality of areas of the object along an inspection path by changing which area of the object is in view of the array by changing a rate of motion for the stage;
    wherein the optical inspection system is configured to operate in at least a base speed mode and at least one N-multiplied speed mode while inspecting the object during the same inspection, wherein the N-multiplied speed mode is a function of the base speed mode multiplied by an integer N;
    wherein, in the base speed mode:
        the stage is configured to change the area in view of the array at a first rate of motion, and the system is configured to image an area using a first number of pixels;
    wherein, in an N-multiplied speed mode:
        the at least one detector is configured to bin at least some pixel elements so that the system images an area using a second number of pixels and the second number of pixels is about equal to the first number of pixels divided by the integer N.

14. The system as set forth in claim 13, wherein the at least one detector is configured to bin at least some pixel elements that are adjacent to one another in a direction parallel to the inspection path.

15. The system as set forth in claim 13, wherein the at least one detector is configured to bin at least some pixel elements that are adjacent to one another in a direction perpendicular to the inspection path.

16. The system as set forth in claim 13, wherein the at least one detector is configured to bin at least some pixel elements that are adjacent to one another in both a direction perpendicular to the inspection path and a direction parallel to the inspection path.

17. A method of inspecting an object, the method comprising:
    accessing data indicating a selection of an inspection speed mode from a set of N-speed modes, the set comprising a base speed and at least one N-speed wherein the N-speed is equal to the base speed multiplied by an integer N and the integer N is greater than 1;
    changing, a rate of motion, of a stage supporting an object wherein an area of the object is in view of an imager, the imager comprising at least one time-delayed integration sensor; and
    imaging a plurality of areas of the object along an inspection path, each area comprising a number of pixels, wherein the number of pixels is about equal to a base number of pixels divided by the integer N,
    wherein the base speed mode is adjusted during an inspection to change from a base speed mode to the at least one N-speed mode.

18. The method as set forth in claim 17, wherein imaging comprises binning at least some pixel elements that are adjacent to one another in a direction parallel to the inspection path.

19. The method as set forth in claim 17, wherein imaging comprises binning at least some pixel elements that are adjacent to one another in a direction perpendicular to the inspection path.

20. The method as set forth in claim 17, wherein imaging comprises binning at least some pixel elements that are adjacent to one another in both a direction perpendicular to the inspection path and a direction parallel to the inspection path.

* * * * *